United States Patent [19]

Kelly

[11] Patent Number: 4,952,703

[45] Date of Patent: Aug. 28, 1990

[54] INTERMEDIATES FOR MAKING 2-OXINDOLE-1-CARBOXAMIDES

[75] Inventor: Sarah E. Kelly, Mystic, Conn.

[73] Assignee: Pfizer Inc., New York, N.Y.

[21] Appl. No.: 357,138

[22] Filed: May 25, 1989

[51] Int. Cl.$^5$ ............... C07D 491/056; C07D 209/42
[52] U.S. Cl. ................... 548/431; 544/333; 544/405; 546/270; 546/273; 548/127; 548/134; 548/136; 548/181; 548/214; 548/235; 548/248; 548/249; 548/336; 548/374; 548/450; 548/466; 548/468; 548/486
[58] Field of Search ............... 548/431, 450, 468, 486

[56] References Cited

U.S. PATENT DOCUMENTS 4,658,037 4/1987 Kadin ................... 548/486
4,665,194 5/1987 Crawford ............. 548/486

OTHER PUBLICATIONS

Graf, Angew. Chem. Internat. Edit. 7, 172–182 (1968).

Primary Examiner—Mary E. Ceperley
Attorney, Agent, or Firm—Peter C. Richardson; J. Trevor Lumb; Gregg C. Benson

[57] ABSTRACT

Preparation of 2-oxindole-1-carboxamides by reaction of 2-oxindoles with trichloracetyl isocyanate to produce novel N-trichloroacetyl-2-oxindole-1-carboxamides which are then hydrolyzed to 2-oxindole-1-carboxamides useful as analgesic and anti-inflammatory agents and/or intermediates for such agents.

11 Claims, No Drawings

INTERMEDIATES FOR MAKING 2-OXINDOLE-1-CARBOXAMIDES

BACKGROUND OF THE INVENTION

1. Field of the Invention

This invention relates to a process for making 2-oxindole-1-carboxamides which comprises reacting a 2-oxindole with trichloroacetyl isocyanate to produce a novel N-trichloroacetyl 2-oxindole-1-carboxamide which is then hydrolyzed to a 2-oxindole-1-carboxamide. The latter compounds are valuable analgesic and antiinflammatory agents and/or useful as intermediates for such agents.

2. Description of Related Art

Graf, Angew. Chem. Internat. Edit. 7, 172–182 (1968) describes addition of amines and carboxamides to chlorosulfonyl isocyanate to produce N-chlorosulfonylureas and acyl N-chlorosulfonylureas, respectively.

U.S. Pat. Nos. 4,652,658 and 4,665,194, issued Mar. 24, 1987 and May 12, 1987, respectively describe a process for making 2-oxindole-1-carboxamides by reacting a 2-oxindole with chlorosulfonyl isocyanate to produce a N-chlorosulfonyl-2-oxindole-1-carboxamide which is then hydrolyzed to a 2-oxindole-1-carboxamide.

U.S. Pat. Nos. 3,634,453; 4,556,672 and 4,569,942, issued Jan. 11, 1972, Dec. 3, 1985 and Feb. 11, 1986, respectively, describe preparation of 2-oxindoles of formula (I) below.

SUMMARY OF THE INVENTION

The present invention relates to a simple process, which is adaptable to a one-pot process, for making 2-oxindole-1-carboxamides in yields and purity at least as good as those obtainable by known methods. The process comprises reacting a 2-oxindole with trichloroacetyl isocyanate to produce a novel N-trichloroacetyl 2-oxindole-1-carboxamide which is then hydrolyzed to a 2-oxindole-1-carboxamide. The process, the intermediate and the final products are presented below:

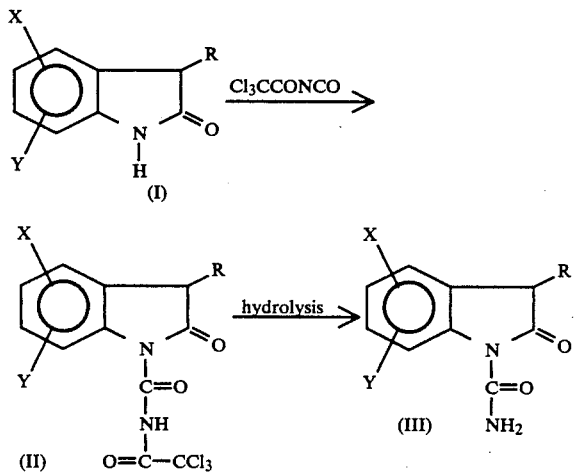

wherein
X is selected from the group consiting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

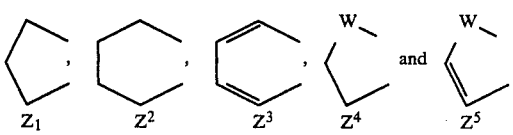

wherein W is oxygen or sulfur;
R is hydrogen or

wherein
$R^I$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and $-(CH_2)_n-Q-R^\circ$;
wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene; and $R^\circ$ is hydrogen or alkyl having 1 to 3 carbons.

Compounds of formula (III) wherein R is hydrogen are useful as intermediates for preparation of analgesic and antiinflammatory compounds wherein R is $-COR^1$ wherein $R^I$ is as defined above.

DETAILED DESCRIPTION OF THE INVENTION

The first step of the process of this invention comprises reacting an appropriate 2-oxindole of formula (I) wherein X, Y and R are as defined above in a reaction-inert solvent at a temperature of from about −20° C. to 150° C. In general, temperatures of from about 20° C. to 110° C. are favored. Higher or lower temperatures can be used if desired. However, temperatures outside the favored temperature range are generally avoided for practical reasons.

By reaction-inert solvent is meant a solvent system which does not react with the reactants or products of the reaction. The term solvent system is used to indicate that a single solvent or a mixture of two or more solvents can be used. Representative solvents are aromatic hydrocarbons such as benzene, toluene, xylene, nitrobenzene, chlorobenzene; aliphatic hydrocarbons such as pentane, hexane; dialkyl ethers such as diethyl ether, diisopropyl ether; chlorinated hydrocarbons such as methylene chloride, dichloroethylene, carbon tetrachloride, chloroform; acetonitrile, acetone and cyclic ethers such as tetrahydrofuran, dioxane; and mixtures thereof. The solvent system used need not bring about complete solution of the reactants.

The 2-oxindole and trichloroacetyl isocyanate are generally reacted in molar proportions ranging from equimolar to 30% excess of trichloroaectyl isocyanate, i.e., 1:1 to 1:1.3. Larger excesses of trichloroacetyl isocyanate appear to afford no advantages and are not used for reasons of economy.

The thus-produced trichloroacetyl derivatives of formula II can be isolated, if desired, or can be converted directly in the same reaction vessel without isolation to formula (III) compounds. Isolation of the intermediate trichloroacetyl compounds of formula (II) is achieved by procedures known to those skilled in the art; e.g. filtration, evaporation of solvent or extraction.

The second step of the process, hydrolysis of the trichloroacetyl derivatives of formula (II), is readily accomplished under acid conditions by treating the formula (II) compounds with an acidic reagent, such as a mineral acid (sulfuric, hydrochloric), camphorsulfonic acid, or toluenesulfonic acid, in the presence of water or an alcohol with or without an additional solvent. Favored solvents are alcohol ($C_{1-4}$) solvents. The preferred alcohol solvent is methanolic solution; silica gel/methanol (or tetrahydrofuran, methylene chloride, or ethyl acetate). The hydrolysis is conducted at a temperature of from about 20° C. to 100° C. and preferably at from about 45° C. to 65° C. The desired 2-oxindole-1-carboxamide is recovered by known methods.

The ratio of acidic reagent to N-trichloroacetyl oxindole-1-carboxamide compound to be hydrolyzed is not critical. In practice, an apparent pH of at least about 3 readily cleaves the trichloroacetyl group. The amount of acidic reagent used for hydrolysis can vary from greater than equimolar quantities to less than equimolar quantities. Molar ratios of acidic reagent to trichloroacetyl compounds of from 0.01:1 to 1:5 are effective in achieving removal of the trichloroacetyl group. Favored acidic reagents are mineral acids, p-toluenesulfonic acid and silica gel. The preferred acidic agent is sulfuric acid in methanol.

When using silica gel as acidic reagent, the trichloroacetyloxindole-1-carboxamide compound is contacted with silica gel in a column or by stirring in a vessel in a suitable solvent. From about 10 grams to about 1,000 grams per mole of trichloroacetyloxindole-1-carboxamide are effective in achieving hydrolysis of the trichloroacetyl group.

The trichloroacetyl isocyanate reactant can be used in premade form or it can be prepared in situ. The in situ preparation comprises reacting trichloroacetyl chloride and potassium cyanate in a reaction-inert solvent such as acetone in a molar ratio of from about 1:1 to 1:5. In practice it is preferred to first react the trichloroacetyl chloride and potassium cyanate in acetone at about room temperature and then to add the oxindole reactant in acetone solution. The reaction is gradually heated to about 50° C. up to the reflux temperature of the solvent until substantially complete as indicated by thin layer chromatography (TLC). The trichloroacetyloxindole carboxamide product can be recovered by known procedures. Alternatively, the trichloroacetyloxindole carboxamide is hydrolyzed in the same reaction vessel by addition of an acidic reagent, preferably sulfuric acid/methanol as described above.

The examples which follow are exemplary of this invention.

EXAMPLE 1

N-Trichloroacetyl 5-Chloro-2-Oxindole-1-Carboxamide

5-Cholor-2-oxindole (5.60 gms, 0.0334 moles) was placed in a flask equipped with a reflux condensor. Touluene (35 ml) was added and the reaction placed in a oil bath under nitrogen. Trichloroacetyl isocyanate (4.78 ml, 0.0400 moles, 1.2 eq.) was added dropwise. The orange colored suspension was slowly warmed to a bath temperature of 80° C. After three hours the reaction was a depp brown-orange color and all solids had dissolved. The solution was concentrated to solids under reduced pressure. The solids were washed with 10 ml of isopropyl alcohol and dried on the funnel to yield the desired trichloroacetyl carboxamide (11.24 gms, 0.0315 moles, 94.5%) as a white solid. m.p.: 166°–168° C. (dec.)

$^1$H NMR (DMSO): 12.64 (s, 1H), 8.02 (d, J=8.9 Hz, 1H), 7.51 (br s, 1H), 7.47 (d, J=8.9 Hz, 1H), 4.02 (s, 2H)

$^{13}$C NMR (DMSO): 178.26, 158.01, 145.93, 138.70, 129.43, 127.71, 126.87, 124.56, 116.86, 91.72, 36.60

MS(EI, DEP): 355.94 (3.43, M+), 353.92 (3.47), 237.02 (3.95), 169.02 (34.64), 168.04 (19.86), 167.04 (100.00), 166.00 (22.18), 139.02 (17.83), 138.00 (13.57), 118.88 (4.08), 116.90 (4.09), 11.98 (5.63), 102.02 (7.83), 75.00 (3.86), 69.98 (12.03)

IR (KBr): 3441 (br, m), 1792 (s), 1782 (s), 1744 (s), 1529 (br, s), 1473 (s), 1369 (m), 1333 (m), 1184 (s), 1144 (s), 818 (s), 752 (s), 717 (m), 660 (s), 619 (s)

HRMS (exact mass): Calcd. 353.9133; found 353.9128

Analysis: Calcd. for $C_{11}H_6N_2O_3Cl_4$: C, 37.11; H, 1.70; N, 7.87; Found: C, 36.78; H, 1.61; N, 7.78.

EXAMPLE 2

N-Trichloroacetyl 5-Fluoro-6-Chloro-2-Oxindole-1-Carboxamide

5-Fluoro-6-chloro-2-oxindole (2.03 g, 0.011 mol) was suspended in 15 mL dry toluene under $N_2$. Trichloroacetylisocyanate (1.57 mL, 0.013 mol) was added and the mixture was heated to reflux for 16 hours. The black solution was cooled to room temperature and concentrated to a brown solid. The solid was slurried in hot isopropanol (10 ml), and filtered. The filtrate was concentrated to a black oil, dissolved in 15 mL·boiling $CHCl_3$, decolorized with charcoal, filtered and crystallized overnight in the freezer. The crystals were collected, washed with cold chloroform and air dried. Yield 1.69 g (41%) off-white crystals. A second recrystallization from chloroform yielded 0.80 g white crystals.

m.p. 145°–146° C.

$^1$H NMR (DMSO): 12.56 (s, 1H), 8.14 (d, J=6.64 Hz), 7.56 (d, J=8.70 Hz), 4.02 (s, 2H)

13C NMR (DMSO): 178.11, 158.00, 154.81 (d, J=244.1 Hz), 145.97, 136.66, 125.90 (d, J=8.75 Hz), 118.23 (d, J=19.02 Hz), 116.90, 113.50 (d, J=24.30 Hz), 91.63, 36.66

MS (EI, DEP): 373.80 (2.27, M+), 254.92 (3.40), 242.92 (2.57), 211.92 (3.60), 186.94 (45.71), 185.94 (22.67), 184.94 (100.00), 183.94 (41.79), 158.96 (10.20), 157.96 (11.73), 156.94 (30.47), 155.94 (34.91), 150.02 (5.51), 129.96 (8.18), 128.94 (3.07), 118.90 (10.11)

HRMS (exact mass): Calcd. 373.9008; found 373.9019

IR (KBr): 3475 cm$^{-1}$(br, w), 1785 (s), 1753 (s), 1716 (m), 1598 (m), 1503 (br, s), 1469 (br, s), 1428 (s), 1292 (m), 1182 (s), 1106 (br, m), 940 (m) 885 (m), 816 (m), 757 (m), 750 (m), 620 (s)

Analysis: Calcd. for $C_{11}H_5N_2O_3Cl_4F$: C, 35.33; H, 1.35; N, 7.49; Found: C, 35.21; H, 1.32; N, 7.40.

EXAMPLE 3

N-Trichloroacetyl 6-Fluoro-2-Oxindole-1-Carboxamide

6-Fluoro-2-oxindole (1.28 g, 8.47 mmol) was suspended in 15 mL dry toluene under $N_2$. Trichloroacetyl isocyanate (1.21 mL, 10.0 mmol) was added and the mixture heated at reflux for 16 hours. The dark brown solution was cooled to room temperature and concentrated to a brown oil on the rotary evaporator. The oil was triturated in 5 mL isopropanol and concentrated to a light brown solid; 3.30 g. The solid (2.26 g) was dissolved in 75 mL boiling chloroform (a small amount of insolubles were present), treated with charcoal and filtered through diatomaceous earth. The filtrate was concentrated to about 20 mL on the steam bath, cooled to room temperature and placed in the freezer overnight. The precipitate was collected, washed with a few mL cold chloroform and vacuum dried. Yield 1.04 g (53%) yellow solid.

m.p. 134°–136.5° C.

$^1$H NMR (DMSO): 12.62 (s, 1H), 7.82 (dd, J=2.34, 10.33 Hz, 1H), 7.43 (m, 1H), 7.12 (m, 1H), 3.97 (s, 2H)

13C NMR (DMSO): 178.96, 161.32 (d, J=240.84 Hz), 158.05, 146.06, 140.78 (d, J=12.49 Hz), 125.77 (d, J=9.46 Hz), 120.46, 111.74 (d, J=22.43 Hz), 103.72 (d, J=30.08), 91.67, 36.22

MS (EI, DEP): 337.92 (2.60, M+), 221.02 (4.80), 209.02 (1.92), 194.04 (5.51), 178.04 (2.91), 152.08 (18.48), 151.10 (100.00), 150.06 (48.26), 149.08 (1.56), 124.02 (6.09), 123.06 (49.45), 122.06 (59.59), 120.98 (5.87)

HRMS (exact mass): Calcd. 337.9428, found 337.9463

IR (KBr): 3386 cm$^{-1}$(w), 1797 (s), 1784 (s), 1742 (s), 1717 (m), 1607 (m), 1520 (br, s), 1354 (s), 1298 (s), 1184 (s), 1130 (s), 1079 (m), 748 (m), 638 (m), 624 (s)

Analysis: Calcd. for $C_{11}H_6N_2O_3Cl_3F$: C, 38.91; H, 1.78; N, 8.25. Found: C, 38.68; H, 1.64; N, 8.05.

EXAMPLE 4

5-Chloro-2-Oxindole-1-Carboxamide

The trichloroacetyl carboxamide of Example 1 (4.56 gms, 0.0128 mmoles) was placed in a flask fitted with a reflux condenser. To the flask was added 30 ml of methanol. Sulfuric acid (0.4 ml) was added dropwise to the reaction. The orange colored slurry was slowly heated to a bath temperature of approximately 45° C. The solution cleared initially and was then followed by precipitation of an off-white solid. After six hours the reaction was cooled and filtered. The solids were washed with 10 ml of cold methanol and dried to yield the desired carboxamide (2.25 gms, 0.0107 moles, 83%) as an off-white solid.

m.p. 208°–210° C. (dec).

$^1$H NMR (DMSO): 8.04 (d, J=8.9 Hz, 1H), 8.00 (br s, 1H), 7.81 (br s, 1H), 7.39 (d, J=1.2 Hz, 1H), 7.32 (dd, J=1.2, 8.9 Hz, 1H), 3.85 (s, 2H)

13C NMR (DMSO): 176.48, 151.95, 140.39, 127.95, 127.23, 126.66, 124.12, 116.71, 36.36

MS(EI, DEP): 210.00 (10.15, M+), 170.04 (2.22), 169.02 (32.23), 168.06 (11.66), 167.04 (100.00), 165.98 (3.66), 141.04 (8.25), 140.04 (15.47), 139.04 (29.58), 138.02 (33.41), 135.08 (2.24), 132.06 (9.55), 114.04 (2.54), 112.04 (9.53)

IR (KBr): 3366 cm$^{-1}$ (m), 1742 (s), 1715 (s), 1584 (s), 1470 (s), 1369 (s), 1354 (s), 1290 (s), 1263 (s), 1206 (m), 1165 (br, m), 1086 (m), 1069 (m), 820 (s), 772 (m), 738 (m), 623 (s), 595 (s), 570 (m), 340 (s)

HRMS (exact mass): Calcd. 210.0196; found 210.0193

EXAMPLE 5

6-Fluoro-2-Oxindole-1-Carboxamide

The product of Example 3 (0.96 g) was suspended in 6 mL methanol. Two drops of concentrated $H_2SO_4$ were added and the mixture refluxed for 3 hours. The mixture was then cooled in an ice/acetone bath and filtered. The solids were washed with 2 mL cold methanol and air dried on the funnel. Yield 0.28 g tan solids (51%).

m.p. 198°–200° C.

$^1$H NMR (DMSO): 7.97 (br s, 1H), 7.81 (m, 2H), 7.32 (m, 1H), 6.96 (m, 1H), 3.80 (s, 2H).

13C NMR (DMSO): 177.23, 161.28 (d, J=239.66 Hz), 151.96, 142.55 (d, J=12.60 Hz), 125.22 (d, J=9.28 Hz), 120.16, 110.15 (d, J=22.41 Hz), 103.49 (d, J=29.88 Hz), 36.06.

MS (EI, DEP): 194.04 (18.95, M+), 152.06 (15.60), 151.06 (100.00), 150.06 (9.25), 124.06 (5.13), 123.06 (58.76), 122.06 (79.24), 108.04 (2.75), 107.04 (6.83)

HRMS (exact mass): Calcd. 194.0502, found 194.0541

IR (KBr): 3380 cm$^{-1}$(s), 1750 (s), 1712 (s), 1578 (m), 1493 (m), 1440 (m), 1364 (s), 1293 (s), 1175 (m), 1082 (m), 1003 (w), 871 (m), 815 (m), 777 (w), 624 (m)

EXAMPLE 6

N-Trichloroacetyl-4-Chloro-5-Fluoro-2-Oxindole-1-Carboxamide

4-Chloro-5-fluoro-2-oxindole (3.59 g, 0.019 mol) was suspended in 30 mL dry toluene under $N_2$. Trichloroacetylisocyanate (2.80 mL, 0.023 mol) was added and the mixture heated to reflux, by which time all solids had dissolved. Reflux was continued for 16 hours. The black solution was allowed to cool to room temperature and then concentrated to an oil on the rotary evaporator. The oil was dissolved in about 50 mL chloroform. Hexane (350 ml) was added with stirring, and the resulting dark brown solids filtered off. The filtrate was concentrated to solids on the rotary evaporator to yield 5.88 g (81%) of the desired trichloroacetyl carboxamide. Further purification was achieved by twice recrystallizing from ethyl acetate.

Orange crystals; m.p. 185°–187° C.

$^1$H NMR (DMSO): 12.53 (s, 1H), 8.00 (dd, J=4.12, 8.98 Hz, 1H), 7.47 (m, 1H), 4.07 (s, 2H)

13C NMR (DMSO): 117.32, 158.01, 154.88 (d, J=245.24 Hz), 145.93, 136.66, 125.857, 116.30 (d,

J=20.34 Hz), 115.847 (d, J=21.47 Hz), 115.38 (d, J=7.9 Hz), 91.62, 36.48

MS(EI, DEP): 373.84 (2.25, M+), 254.96 (2.01), 243.98 (1.85), 242.96 (10.30), 211.96 (3.66), 210.96 (2.13), 208.00 (12.40), 187.96 (3.47), 186.96 (34.15), 185.98 (20.86), 184.96 (100.00), 183.96 (42.33), 158.98 (10.78), 157.98 (10.51), 156.98 (32.47), 155.96 (26.88), 150.04 (3.24), 129.96 (9.74), 120.98 (11.52), 120.02 (10.02), 118.92 (10.39), 116.90 (9.28)

HRMS (exact mass): Calcd. 373.9009, found 373.9002
IR (KBr): 3422 cm$^{-1}$ (br, w), 1793 (s), 1758 (m), 1747 (s), 1715 (m), 1603 (m), 1508 (br, s), 1470 (s), 1454 (s), 1282 (s), 1253 (s), 1233 (s), 1174 (s), 1138 (s), 1120 (s), 842 (s).

EXAMPLE 7

6-Chloro-5-Fluoro-2-Oxindole-1-Carboxamide

6-Chloro-5-fluoro-2-oxindole (0.36 g, 1.95 mmol) was suspended in 10 mL dry toluene under N$_2$. Trichloroacetylisocyanate (279 μL, 2.34 mmol) was added and the mixture was heated at reflux for 16 hours. The black solution was cooled to room temperature, concentrated on the rotary evaporator to solids, suspended in 5 mL methanol and 2 drops concentrated H$_2$SO$_4$, and heated at reflux for 3 hours. The resulting mixture was cooled in an ice/acetone bath and filtered. The solids were washed with 2 mL cold methanol and vacuum dried. Yield 0.29 g of light brown solids (65%).

m.p. 215.5°-217° C.

$^1$H NMR (DMSO): 8.13 (d, J=6.8 Hz, 1H), 7.93 (br s, 1H), 7.84 (br s, 1H), 7.43 (d, J=8.7, 1H), 3.84 (s, 2H)

$^{13}$C NMR (DMSO): 176.37, 154.04 (d, J=242.68 Hz), 151.87, 138.31, 125.57 (d, J=8.2 Hz), 117.70 (d, J=18.79 Hz), 116.59, 113.03 (d, J=24.37 Hz), 36.51

MS(EI, DEP): 228.02 (9.54, M+), 217.02 (2.27), 188.04 (3.70), 187.02 (31.90), 186.04 (11.36), 185.00 (100.00), 184.00 (6.70), 160.02 (3.26), 159.02 (10.41), 158.02 (20.56), 157.00 (28.96), 156.02 (48.88), 150.06 (5.63), 132.00 (4.09), 131.00 (1.98), 130.00 (9.79), 128.88 (2.32)

HRMS (exact mass): Calcd 228.0102, found 228.0108
IR (KBr): 3389 cm$^{-1}$ (s), 1750 (s), 1717 (s), 1592 (s), 1468 (s), 1287 (s), 1175 (m), 1090 (m), 1004 (m), 875 (m), 772 (br, m), 717 (m), 638 (s).

EXAMPLE 8

4-Chloro-5-Fluoro-2-Oxindole-1-Carboxamide

4-Chloro-5-fluoro-2-oxindole (0.23 g, 1.25 mmol) was suspended in 6 mL dry toluene under N$_2$. Trichloroacetylisocyanate (0.18 mL, 1.50 mmol) was added and the mixture heated at reflux for 16 hours. The black solution was cooled and concentrated on the rotary evaporator to solids. The brown solids were suspended in 6 mL methanol plus 2 drops of concentrated H$_2$SO$_4$ and the mixture heated at reflux for 3 hours. The mixture was cooled in an ice/acetone bath, filtered, and the solid washed with 2 mL cold methanol and vacuum dried. Yield 0.19 g (68%) tan solids.

m.p. 196°-198° C.

$^1$H NMR (DMSO): 7.99 (dd, J=4.24, 8.99 Hz, 1H), 7.93 (br s, 1H), 7.85 (br s, 1H), 7.33 (m, 1H), 3.88 (s, 2H)

$^{13}$C NMR (DMSO): 175.57, 154.06 (d, J=242.53 Hz), 151.83, 138.35, 125.51, 115.81 (d, J=20.37 Hz), 115.18 (d, J=21.51 Hz), 114.99 (d, J=6.87 Hz), 36.33

MS(EI, DEP): 227.96 (11.82, M+), 187.96 (3.64), 186 94 (37.93), 185.96 (11.53), 184.94 (100.00), 183.94 (5.85), 158.96 (15.45), 157.96 (15.84), 156.96 (46.01), 155.96 (46.85), 150.02 (4.82), 131.96 (6.06), 130.98 (2.29), 129.96 (14.98), 128.94 (2.81), 122.02 (7.86), 120.98 (7.10), 120.00 (6.77)

HRMS (exact mass): Calcd 228.0102, found 228.0076
IR (KBr): 3737 cm$^{-1}$ (m), 1786 (w), 1734 (s), 1716 (m), 1589 (m), 1471 (s), 1454 (m), 1359 (s), 1283 (m), 1250 (m), 1167 (m), 1107 (br, m), 831 (m), 743 (m), 632 (m), 586 (m).

EXAMPLE 9

5-Chloro-3-(2-Thenoyl)-2-Oxindole-1-Carboxamides

A. N-Trichloroacetyl-5-chloro-3-(2-thenoyl)-2-oxindole-1-carboxamide

5-Chloro-3-(2-thenoyl)-2-oxindole (202 mg, 0.688 mmol), toluene (8 mL) and trichloroacetyl isocyanate (98 μL, 0.825 mmol) were refluxed overnight under a nitrogen atmosphere. The reaction was concentrated under reduced pressure to a yellow solid. Recrystallization of the solid from chloroform (5 mL) gave 188 mg (63%) of the N-trichloroacetyl derivative.

B. Hydrolysis of N-trichloroacetyl derivative

The product from part A above was suspended in methanol (1.5 mL) and sulfuric acid (1 drop) added. The reaction was refluxed for three hours, cooled to room temperature, and then cooled further in an ice bath. The solid which separated was recovered by filtration, washed with cold methanol and air-dried. Yield=61 mg (77%) of the deacylated product. Overall yield of steps A and B=48%.

The following compounds are prepared from appropriate reactants according to the procedure of Example 1.

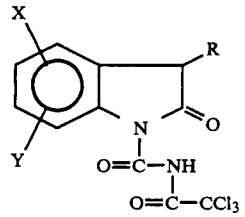

| X | Y | R |
|---|---|---|
| H | H | H |
| 5-CH$_3$ | 6-F | H |
| H | 5-Br | H |
| 5-CH$_3$ | H | H |
| 5-CH$_3$ | 6-CH$_3$ | H |
| 5-OCH$_3$ | H | H |
| 6-Cl | H | H |
| H | 5-CF$_3$ | H |
| 5-O-n-C$_4$H$_9$ | H | H |
| 5-S-n-C$_4$H$_9$ | H | H |
| 6-n-SO$_2$C$_4$H$_9$ | H | H |
| 6-n-SOC$_4$H$_9$ | H | H |
| 5-SO$_2$N(CH$_3$)$_2$ | H | H |
| 5-SO$_2$N(n-C$_3$H$_7$)$_2$ | H | H |
| 4-SCH$_3$ | H | H |
| 5-F | 6-F | H |
| 5-NO$_2$ | H | H |
| 5-OCH$_3$ | 6-OCH$_3$ | H |
| 6-C$_6$H$_5$ | H | H |
| 5-Cl | 6-Cl | H |
| 5-COCH$_3$ | H | H |
| 5-benzoyl | H | H |
| 5-(2-thenoyl) | H | H |
| H | 5-i-C$_3$H$_7$ | H |
| H | 6-O-n-C$_4$H$_9$ | H |
| H | 4-SCH$_3$ | H |
| 5-C$_6$H$_{11}$ | H | H |
| H | 6-C$_3$H$_5$ | H |

-continued

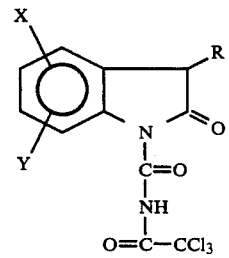

| X | Y | R |
|---|---|---|
| 5,6-O—CH₂—O— | | H |
| 4,5-CH₂CH₂CH₂— | | H |
| 5,6-CH=CH—CH=CH— | | H |
| 6,7-CH₂CH₂CH₂CH₂— | | H |
| 5,6-O—CH₂—CH₂— | | H |
| 5,6-CH₂—CH₂—O— | | H |
| 5,6-S—CH₂—CH₂— | | H |
| 6-Cl | H | 2-thenoyl |
| 5-Cl | H | 2-thenoyl |
| H | 5-CF₃ | 2-thenoyl |
| 5-Cl | 6-Cl | 2-furoyl |
| 5-OCH₃ | H | acetyl |
| 4-Cl | H | sec-butyryl |
| 5-NO₂ | H | C₆H₅CO |
| 4-Cl | H | C₆H₁₁CO |
| 6-Cl | H | C₄H₉CO |
| 5-F | H | bicyclo[2.2.1]heptan-2-yl-2-yl-CO |
| 5-Cl | H | bicyclo[2.2.1]hept-2-en-5-5-yl-CO |
| 5-CF₃ | H | C₆H₅CO |
| H | H | C₆H₅CO |
| 5-F | 6-Cl | 2-thenoyl |
| H | 5-Cl | 3-thenoyl |
| 5,6-CH=CH—S— | | 2-furoyl |
| 5,6-O—CH₂—CH₂—O— | | 2-thenoyl |
| 6,7-O—CH₂—CH₂—O— | | 2-thenoyl |
| 6-C₃H₅ | H | 4-ClC₆H₄CO |
| 5-C₆H₁₁ | H | C₆H₅CH₂CO |
| 5-CH(CH₃)₂ | H | 3-methyl-2-thenoyl |
| 5-F | 6-Cl | 5-n-propyl-2-thenoyl |
| 5-Cl | H | 1-naphthoyl |
| H | 5-Br | 3-(2-tolyl propionyl) |
| 6-n-C₃H₇CO | H | CO-(4-isothiazolyl) |
| 6-CF₃ | H | (4-thiazolyl)acetyl |
| 5-SO₂N(n-C₃H₇)₂ | H | CO-(2-tetrahydrofuryl) |
| H— | 4-Cl | CO-(4-pyridyl) |
| H | H | CO-(5-pyrimidyl) |
| 5-CH₃ | 6-F | CO-(2-pyrazinyl) |
| H | H | CO-(3-isoxazolyl) |
| 5-C₆H₅CONH | H | 2-thenoyl |
| 5-CH₃CONH | H | 3-phenyl propionyl |
| 5-Br | H | CO-(2-oxazolyl) |
| H | 6F | C₆H₅CH₂CO |
| 5-C₄H₃SCO | H | 3-(3-chlorophenyl)butyryl |
| 5-C₆H₅CO | H | CO-(1,2,3-thiadiazol-4-yl) |
| 5-Cl | H | CO-(2-tetrahydrothienyl) |
| 5-Cl | H | 2-pyrroyl |
| 6-CF₃ | H | 2-phenoxy propionyl |
| 6-F | H | thiophenoxyacetyl |
| 5-F | 6-Cl | CO-(2-tetrahydropyranyl) |
| 5-CF₃ | H | CO-(3-imidazolyl) |
| H | 6-CF₃ | CO-(2-pyrazolyl) |
| H | 5-OC₂H₅ | CO-(2-tetrahydrothio)pyranyl) |

EXAMPLE 11

Following the procedure of Example 4, the N-trichloraecetyl compounds of Example 10 are hydrolyzed to their corresponding carboxamides having the formula below wherein X, Y and R are as defined in Example 10

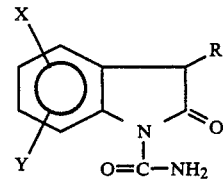

I claim:
1. A compound of the formula (II)

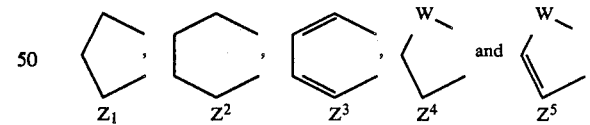

wherein
X is selected from the group consisting of hydorgen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;
or X and Y when taken together are a 4,5-, 5,6- or 6,7-methylenedioxy group or a 4,5-, 5,6- or 6,7-ethylenedioxy group;
or X and Y when taken together and when attached to adjacent carbon atoms, form a divalent radical Z, wherein Z is selected from the goups consisting of

wherein W is oxygen or sulfur;
R is hydrogen or $$-\overset{O}{\underset{\|}{C}}-R^1$$

wherein
R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons is said alkyl, (substituted phenoxyl)alkyl having 1 to 3 carbons in said alkyl, (thiophenoxy)-alkyl having 1 to 3 carbons in said alkyl, naphthyl, bicyclo[2,2,1]heptan-2yl and bicyclo[2.2.1-]hept-5-en-2-yl;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and 2. A compound according to claim 1 wherein R is hydrogen.

3. A compound according to claim 2 wherein X is hydrogen, fluoro, chloro or trifluoromethyl; and Y is hydrogen, fluoro, chloro or trifluoromethyl.

4. A compound according to claim 3 wherein Y is hydrogen and X is located at the 5- or 6-position and is chloro, fluoro or trifluoromethyl.

5. A compound according to claim 4 wherein X is at the 6-position.

6. The compound according to claim 5 wherein X is 6-chloro.

7. The compound according to claim 5 wherein X is 6-trifluoromethyl.

8. The compound according to claim 5 wherein X is 6-fluoro.

9. A compound according to claim 3 wherein X is 5-chloro or 5-fluoro; and Y is 6-chloro or 6-fluoro.

10. The compound according to claim 9 wherein X is 5-chloro and Y is 6-chloro.

11. The compound according to claim 9 wherein X is 5-fluoro and Y is 6-chloro.

* * * * *

UNITED STATES PATENT AND TRADEMARK OFFICE
CERTIFICATE OF CORRECTION

PATENT NO. : 4,952,703
DATED : August 28, 1990
INVENTOR(S) : Sarah E. Kelly

It is certified that error appears in the above-identified patent and that said Letters Patent is hereby corrected as shown below:

Column 4, line 42 - "11.98" should read -- 111.98 --;

Column 8, line 32 - before "The following compounds" insert -- EXAMPLE 10 --;

Column 10, line 45 - "goups" should read -- group --; and

Column 11, line 11 - after "and" insert --trifluoromethyl.--."

Signed and Sealed this

Eleventh Day of August, 1992

*Attest:*

DOUGLAS B. COMER

*Attesting Officer*   Acting Commissioner of Patents and Trademarks